(12) United States Patent
Klee et al.

(10) Patent No.: US 11,089,998 B2
(45) Date of Patent: Aug. 17, 2021

(54) SYSTEM FOR INCREASING A PATIENT'S COMPLIANCE WITH A THERAPY RELATING TO AN UPPER AIRWAY DISORDER

(71) Applicant: KONINKLIJKE PHILIPS N.V., Eindhoven (NL)

(72) Inventors: Mareike Klee, Straelen (DE); Jacob Roger Haartsen, Eindhoven (NL); Mark Steven Aloia, Boulder, CO (US); Richard Andrew Sofranko, Pittsburgh, PA (US); David Smith, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 291 days.

(21) Appl. No.: 15/574,598

(22) PCT Filed: May 11, 2016

(86) PCT No.: PCT/EP2016/060583
§ 371 (c)(1),
(2) Date: Nov. 16, 2017

(87) PCT Pub. No.: WO2016/192941
PCT Pub. Date: Dec. 8, 2016

(65) Prior Publication Data
US 2018/0199882 A1 Jul. 19, 2018

Related U.S. Application Data

(60) Provisional application No. 62/167,975, filed on May 29, 2015.

(51) Int. Cl.
*A61B 5/00* (2006.01)
*A61M 16/06* (2006.01)
*A61M 16/00* (2006.01)

(52) U.S. Cl.
CPC .......... *A61B 5/4836* (2013.01); *A61B 5/4818* (2013.01); *A61B 5/6803* (2013.01);
(Continued)

(58) Field of Classification Search
CPC ....... A61B 5/00; A61B 5/0002; A61B 5/0015; A61B 5/68; A61B 5/6801; A61B 5/4836;
(Continued)

(56) References Cited

U.S. PATENT DOCUMENTS 7,787,946 B2 * 8/2010 Stahmann ............ A61B 5/0031
607/3
7,958,892 B2 6/2011 Kwok et al.
(Continued)

FOREIGN PATENT DOCUMENTS

EP 2008581 A2 12/2008
WO 2008070148 A1 6/2008
(Continued)

OTHER PUBLICATIONS

King, J., Kupferthaler, A., Frauscher, B., Hackner, H., Unterkofler, K., Teschl, G., . . . & Högl, B. (2012). Measurement of endogenous acetone and isoprene in exhaled breath during sleep. Physiological measurement, 33(3), 413. (Year: 2012).*

*Primary Examiner* — Christian Jang (57) ABSTRACT

A device and method for increasing a patient's compliance with a therapy relating to an upper airway disorder includes a receiving unit, a processing unit, and a display unit. The receiving unit is configured to receive vital sign data including glucose level data of the patient, and therapy data including information regarding the therapy of the patient. The processing unit is configured to process the therapy data and the vital sign data in order to determine feedback information based on the therapy data and the vital sign data.

(Continued)

Lastly, the display unit is configured to display the feedback information based on the therapy data and the vital sign data.

13 Claims, 6 Drawing Sheets

(52) U.S. Cl.
CPC .......... *A61M 16/024* (2017.08); *A61M 16/06* (2013.01); *A61M 16/0655* (2014.02); *A61M 16/0683* (2013.01); *A61B 5/6802* (2013.01); *A61B 5/6813* (2013.01); *A61M 2205/502* (2013.01); *A61M 2230/04* (2013.01); *A61M 2230/06* (2013.01); *A61M 2230/201* (2013.01); *A61M 2230/30* (2013.01)

(58) Field of Classification Search
CPC ... A61B 5/6803; A61B 5/4818; A61B 5/6813; A61B 5/6802; A61M 16/00; A61M 16/06; A61M 16/021; A61M 16/022; A61M 16/024; A61M 16/026; A61M 16/0605; A61M 16/0633; A61M 16/0644; A61M 16/0655; A61M 16/0683; A61M 2230/06; A61M 2230/04; A61M 2230/30; A61M 2230/201; A61M 2205/50

See application file for complete search history.

(56) References Cited

U.S. PATENT DOCUMENTS

| | | | |
|---|---|---|---|
| 9,463,294 | B2 | 10/2016 | Laura |
| 9,814,850 | B2 | 11/2017 | Paul |
| 2005/0061315 | A1 | 3/2005 | Lee et al. |
| 2005/0188991 | A1* | 9/2005 | Sun .............. A61B 5/0002 |
| | | | 128/204.23 |
| 2011/0132370 | A1 | 6/2011 | Farrugia |
| 2014/0137870 | A1 | 5/2014 | Barlow et al. |
| 2014/0144431 | A1 | 5/2014 | Darkin et al. |

FOREIGN PATENT DOCUMENTS

| | | |
|---|---|---|
| WO | 2009109013 A1 | 9/2009 |
| WO | 2015062897 A1 | 5/2015 |
| WO | 2015063247 A1 | 5/2015 |

* cited by examiner

SYSTEM FOR INCREASING A PATIENT'S COMPLIANCE WITH A THERAPY RELATING TO AN UPPER AIRWAY DISORDER

CROSS-REFERENCE TO PRIOR APPLICATIONS

This application is the U.S. National Phase application under 35 U.S.C. § 371 of International Application Serial No. PCT/EP2016/060583 filed on 11 May 2016, which claims the benefit of U.S. Application Ser. No. 62/167,975, filed on 29 May 2016 and European Application No. 15172945.6, filed on 19 Jun. 2015. These applications are hereby incorporated by reference herein.

FIELD OF THE INVENTION

The present invention pertains to increasing patients' compliance with a therapy relating to an upper airway disorder. In particular, a device and a method are disclosed wherein feedback information are provided to the patient, thereby increasing his/her therapy compliance.

BACKGROUND OF THE INVENTION

Upper respiratory diseases are spread in society. Examples of such upper respiratory diseases comprise infections of the upper respiratory tract, asthma, neuromuscular disorders, chronic obstructive pulmonary disease (COPD) and obstructive sleep apnea (OSA). A common medical approach for treatment or ailment of symptoms of the above-mentioned diseases comprises ventilation therapy. Ventilation therapy encompasses invasive ventilation, such as intubation, and non-invasive approaches, including pressure therapy, such as positive airway pressure (PAP) therapy.

Especially from OSA and diabetes it is known that these disorders often coexist.

OSA is usually caused by an obstruction of the upper airway. It is characterized by repetitive pauses in breathing during sleep and is usually associated with a reduction in blood oxygen saturation. These pauses in breathing, called apneas, typically last 20 to 40 seconds. The obstruction of the upper airway is usually caused by a reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages.

Diabetes refers to a group of metabolic diseases characterized by a high blood sugar level over a prolonged period. Diabetes may cause several acute complications including diabetic ketoacidosis and nonketotic hyperosmolar coma and long-term complications, such as cardiovascular disease, stroke, kidney failure and eye damages.

OSA is one of the most common diseases, with a high incidence and prevalence rate that parallels with increasing obesity globally (Salim R Surani *World J Diabetes* 2014 Jun. 15; 5(3): 381-384). Obstructive sleep apnea has been independently linked with e.g. hypertension, atrial fibrillation, cardiac disease, diabetes, insulin resistance, and coronary artery disease (CAD).

One explanation for this overlap of OSA and diabetes is the presence of shared risk factors such as obesity. There may be also a more complex relationship between these conditions in which an underlying metabolic disorder predisposes to both or in which metabolic and autonomic abnormalities associated with one of the two diseases influences the development of the other. Because both diabetes and OSA are associated with increased cardiovascular morbidity and mortality, it is possible that the presence of both conditions results in additive or even synergistic health risks. It has been found that continuous positive airway pressure (CPAP) therapy commonly used for the treatment of OSA and COPD may reduce glucose levels and may also improve morning glycaemic control in type 2 diabetics who suffer from OSA. In a study it has been shown that one week of optimal CPAP use lowered the average 24-hour glucose and improved the post-breakfast glucose response. The dawn phenomenon, an early-morning increase in blood sugar in people who have type 2 diabetics, also was reduced as a result of CPAP therapy. It may be therefore expected that CPAP treatment of sleep apnea across the entire night might improve glucose control and might have at least in some patients as much of an effect as in oral anti-diabetic medication.

It has been furthermore suggested that sleep apnea, sharply raises the risk of type 2 diabetes. More severe cases of sleep apnea are generally associated with poorer blood sugar control in diabetics. While breathing pauses can occur throughout the night in apnea patients, it has been found that episodes that occurred during the rapid eye movement (REM) phase of sleep had the most detrimental effects on long-term blood sugar control. Most REM sleep occurs in the early morning hours before waking. Many patients remove their CPAP mask during night because it can feel uncomfortable. As a result, their apnea is more likely to go untreated during REM sleep, a time that may be particularly important for anyone with diabetes. Accordingly, adherence to sleep therapy is of high relevance for patients with diabetes who suffer also from obstructive sleep apnea and other upper airway disorders.

Devices for treating a patient with both sleep-disorder breathing and diabetes are known e.g. from US 2014/0144431. The device provides a supply of air at positive pressure to the patient. Glycaemia abnormality events are detected and upon detection of such an event an alarm is triggered. WO 2009/109013 A1 discloses blood glucose regulation through control of breathing.

WO 2015/063247 discloses a therapy system with a patient interface for obtaining a vital state of a patient. The system provides information on the vital state of the patient which may be used as an educative tool that links patient lifestyle and apnea occurrence frequency.

WO 2015/062897 discloses a patient feedback system providing feedback information inter alia based on personal profile data. Feedback information may include deviations of the therapeutic device settings of a patient from the reference device settings of reference patients. Personal profile data may include vital sign data and a sleep profile of the patient.

US 2005/0061315 discloses a feedback system and method for sleep disordered breathing therapy. Patient conditions are monitored and used for developing feedback information for controlling sleep disordered breathing therapy based on the one or more monitored conditions. The feedback information is provided to a device delivering therapy to treat sleep disordered breathing.

WO 2008/070148 discloses a pressure support device with a dry electrode sleep staging device for treating sleep apnea. A sleep stage of a user is determined based on EEG signals detected by a dry electrode.

Upper respiratory diseases may further coexist with variations of heart rate, blood pressure and/or impaired sleep quality due to medical reasons.

Main problems still reside in the fact that the known devices diagnose acute health problems and/or provide treatment, but do not alter or influence an incorrect and possibly unambitious usage of a therapy. The devices of the prior art do not address non-compliance of therapies relating to sleep disorder breathing or inadequate compliance with such therapies.

SUMMARY OF THE INVENTION

The present invention deals with overcoming the above-mentioned defects of the state of the art.

In particular, it is an object of the present invention to provide a simple, accurate and efficient device and method for increasing a patient's compliance with a therapy relating to an upper airway disorder. Another object of the present invention is the provision of a device for increasing a patient's compliance with a therapy relating to an upper airway disorder which is easy to operate. Still another object is the provision of a device for monitoring individual's vital signs, such as glucose level, and the usage of a therapy relating to an upper airway disorder, such as sleep therapy, at the same time. Still a further object is the provision of a device which improves incorrect usage of therapy regimen, therapy systems and devices.

In one embodiment, a device for increasing a patient's compliance with a therapy relating to an upper airway disorder is provided. Said device comprises:
  a receiving unit for receiving vital sign data including one or more of glucose level data and norepinephrine level data of the patient, and therapy data including information regarding the therapy of the patient;
  a processing unit configured to process the therapy data and the vital sign data in order to determine feedback information based on the therapy data and the vital sign data; and
  a display unit for displaying the feedback information based on the therapy data and the vital sign data.

In a further embodiment a therapy system comprising the present device is provided.

In another embodiment, a method for increasing patients' compliance with a therapy relating to an upper airway disorder is provided. Said method comprises:
  receiving vital sign data including one or more of glucose level data and norepinephrine level data of the patient, and therapy data including information regarding the therapy of the patient;
  processing the therapy data and the vital sign data in order to determine feedback information based on the therapy data and the vital sign data; and
  displaying the feedback information based on the therapy data and the vital sign data.

According to yet another embodiment of the present invention, a computer program comprising program code means for causing a computer to carry out the present method is provided, when said computer program is carried out on the computer.

Preferred embodiments of the invention are defined in the dependent claims. It shall be understood that the claimed method and computer program have similar and/or identical preferred embodiments as the claimed device and as defined in the dependent claims.

The invention overcomes the above-mentioned disadvantages of the state of the art by displaying feedback information to patients receiving a therapy relating to an upper airway disorder, such a PAP and/or CPAP therapy. The feedback information takes use of a linkage between upper airway disorders and abnormal vital signs, including for instance abnormal glucose levels, such as glucose levels in patients suffering from type 2 diabetes. In the light of the linkage it may be reasonably assumed that a therapy relating to an upper airway disorder, such as a non-invasive ventilation therapy and particularly a positive airway pressure (PAP) therapy and/or CPAP therapy, positively affects vital signs of the patient in general. The vital signs include one or more of glucose level and norepinephrine level data, and optionally heart rate data, blood pressure data and sleep stage data. Glucose levels, particularly blood glucose levels, are preferred vital signs.

Norepinephrine levels, which may be monitored in the blood of the patients, are known to go down with continuous CPAP therapy. It is further known that physiological elevation of norepinephrine impairs insulin sensitivity, but does not influence insulin secretion.

The glucose level data may comprise any kind of data related to and/or reflecting glucose level of the patient. In line with this, the glucose level data may include one or more data on overall glucose response, fasting glucose level, 2 hour glucose level, insulin levels, insulin sensitivity and/or insulin secretion.

Sleep stage data may include not only information about the sleep stages of the patient, such as time intervals between different sleep stages and/or duration of the sleep stages, but also general information about sleep quality, such as objective assessment by another person and/or subjective assessment by the patient. Hence, sleep stage data may be regarded comprising sleep quality data.

The feedback information provided to the patient is based on therapy data and vital sign data. The provision of feedback information increases patients' compliance with the therapy as the patients are taught about and pointed to beneficial effects of the therapy on vital sign data, such as positive glucose level data. One or more vital sign, such as glucose level, during night and the usage of the therapy relating to an upper airway disorder may be monitored and communicated to the patients using an appropriate display unit, such as a smartphone.

The presented device and method may be particularly suitable for patients suffering from sleep apnea and/or other respiratory diseases with non-invasive ventilation, e.g. neuromuscular disorders. The present device may demonstrate the patient the glucose level data from any time period, such as night to night, and/or the related usage of the therapy relating to an upper airway disorder. Thereby, the patient's compliance to the therapy may be increased. Since patient compliance is beneficial to patients suffering from abnormal glucose level (by improving blood glucose levels), medication, including inter alia dosage and therapy regimen, may be lowered. The present device may likewise demonstrate the patient the heart rate data, blood pressure data and sleep stage data from any time period, and/or the related usage of the therapy relating to an upper airway disorder for increasing the patient's compliance to the therapy.

In contrast to US 2014/0144431 or WO 2009/109013 A1, the present system and method provide feedback information to the patient based on the therapy data and the vital sign data. In particular, combining therapy data and vital sign data is not mentioned.

The term "patient compliance", also denominated patient adherence and capacitance, is used for describing the degree to which a patient correctly follows medical advice. In the present case this refers to the degree to which a patient correctly follows the therapy relating to an upper airway disorder or the use of said therapy. Patient compliance is of utmost importance since non-compliance is a major obstacle for an effective delivery of healthcare.

The treatment of patients with a therapy, such as OSA or COPD therapy, normally requires adherence of the patient to the therapy system for defined and usually prolonged time. This is often uncomfortable as the masks used in the therapy system disturb during night. Increasing a patient's compliance thereby preliminarily aims to a more correct use of the therapy relating to an upper airway disorder. For instance, increased patient's compliance resides in that the therapy system is used for a longer time period in comparison to a patient not using the present device. Increasing a patient's compliance may refer to a time period which has been increased at least by 5%, preferably at least by 25%, such as 50%, 80%, 100% or even longer, depending on the adherence of the patient to the therapy relating to an upper airway disorder without using the present device. Alternatively or in addition, increasing a patient's compliance may aim to a more regular use of the device.

An "upper airway disorder" as used herein refers to any disorder of the upper respiratory tract. Examples of upper airway disorders include infections of the upper airway tract, asthma, neuromuscular disorders, COPD and sleep disorder breathing such as obstructive sleep apnea (OSA). Neuromuscular disorders relate to any disease impairing the functioning of the muscles, either directly, being pathologies of the muscle, or indirectly, being pathologies of nerves or neuromuscular junctions. Neuromuscular disorders, COPD and sleep disorder breathing, e.g. OSA, are being preferred since regular treatment often requires the use of ventilation therapy.

Neuromuscular disorders encompass for instance cerebrovascular accident (stroke), Parkinson's disease, multiple sclerosis, Huntington's disease (Huntington's chorea) and Creutzfeldt-Jakob disease, spinal muscular atrophies, amyotrophic lateral sclerosis, neuropathies, neuromuscular junction disorders such as Myasthenia gravis and Lambert-Eaton syndrome, and myopathic disorders such as muscular dystrophies and inflammatory myopathies including polymyositis.

In general, any upper airway disorder which may be treated with ventilation therapy, particularly non-invasive ventilation therapy such as PAP therapy, is preferred. More preferably, the upper airway disorder is obstructive sleep apnea.

"Therapy data" include all data which may be measured and/or determined along therapy and data relating to controlling the device used for therapy. Preferred therapy data include one or more of the Apnea-Hypopnea-Index (AHI), overall sleep apnea severity score, number of apneas and/or apopneas per time unit, e.g. by night, and time of usage of a therapy device for providing said therapy, fit of mask but any other parameters might be also included. The AHI is an index used to indicate the severity of sleep apnea. It is represented by the number of apnea and hypopnea events per hour of sleep. The apneas (pauses in breathing) must last for at least 10 seconds and are associated with a decrease in blood oxygenation. Combining AHI and oxygen desaturation gives an overall sleep apnea severity score that evaluates both number sleep disruptions and degree of oxygen desaturation (low blood level). Therapy data may particularly include information about conscious or unconscious removal of a therapy device, such as a patient-contacting element used for providing PAP therapy.

Therapy data may also encompass medical data and/or behavioral data of the patient. Examples for therapy data may include one or more of the pressure of the breathing gas provided to the patient, time periods of using the device and information relating to particular breathing events, such an incidents of hypopnea and apopnea. Medical data may include any information from the patient's health records. Examples of behavioral data include subjective and objective behavioral data, including for instance self-assessment of the patients about their compliance with the therapy and/or assessment of patients' compliance by another person, such as a medical practitioner or a relative. Behavioral data may also include patient information to their live style, e.g. information about the frequency, such as daily or weekly, of alcohol consume, smoking, physical activities, nutrition derived from dedicated questionnaires. Additional patient data received for example from questionnaires may be comprised in the therapy data as well.

Alternatively or in addition, other patient data from e.g. medical records, such as a blood analysis, may include prior vital sign data. Such prior vital sign data refer to data which have been previously determined and recorded. Prior vital sign data may comprise one or more of prior glucose level data, prior norepinephrine level data, prior heart rate data, prior blood pressure data and prior sleep stage data of the patient. The prior glucose level data may encompass one or more data on overall glucose response, fasting glucose level, 2 hour glucose level, insulin levels, insulin sensitivity, and/or insulin secretion from oral glucose tolerance tests or intravenous glucose tolerance test. It will be appreciated that the prior vital sign data may be obtained by previous use of the present system or method and collecting respective data.

"Feedback information" refer to all kind of information provided to the patient and which have been provided with the intention to increase patients' compliance with the therapy relating to the upper airway disorder. Feedback information preferably encompasses information regarding the progress and effort of the therapy. This may encompass a therapy objective. The therapy objective may be defined in terms of the therapy relating to an upper airway disorder or additionally comprise target values for one or more of vital sign data, daily therapy usage, smoking, alcohol consume, daily nutrition, drugs, and daily physical activity. Preferably, target values for glucose levels or blood glucose levels are provided. It is also preferred that target values for alcohol consume and/or smoking are provided. This is of particular interest as alcohol consume and smoking effect sleep apnea in a negative way.

The feedback information may further encompass statistical information about the time period the patient has used the underlying therapy and correlating of the same with vital sign information, such as glucose level information. Accordingly, the feedback information provided reflects the benefit of the usage of the therapy relating to an upper airway disorder with any of the vital sign data monitored, preferably with respect to glucose level data. For instance, the patient may derive from the patient's instructions provided his/her adherence to the device shown in conjunction with information relating to the proper use of the device, specifically with respect to monitored vital signs. The patient's instructions may also comprise information on the usage of the therapy. In particular, the patient may be informed about predicted vital sign data upon proper use of the device in comparison to the actual use and measured vital signs. The feedback information may comprise any information about too short, irregular and/or wrong usage of the therapy and the effect thereof on vital sign data, such as glucose level data.

According to an embodiment of the present invention the vital sign data further include one or more of heart rate data, blood pressure data and sleep stage data of the patient.

It will be appreciated that there is no limitation with respect to kind of the vital sign data employed in the present device and method, including for instance glucose level data alone or norepinephrine level data alone. Alternatively, a combination of vital sign data may be used, including for instance glucose level data and heart rate data, glucose level data and blood pressure data, glucose level data and sleep stage data, heart rate data and blood pressure data, heart rate data and sleep stage data, blood pressure data and sleep stage data, and a combination of glucose level data, heart rate data, blood pressure data and sleep stage data.

According to one embodiment of the present invention, the therapy data include one or more of an Apnea-Hypopnea-Index (AHI), a number of apneas and/or hypopneas per night, and a time of usage of a therapy device, fit of mask for providing said therapy.

The number of apneas and/or hypopneas may be further provided for any time period including for instance one night and a succession of several nights, such as 2, 3, 4, 5, 6 or 7 nights. The time period may also cover several weeks, including 2, 3, 4, 5, 6, 7 weeks, or several months, such as 2, 3, 4, 5, 6, 12 months or more. The time of usage of a therapy device for providing said therapy may encompass a succession of several nights, such as 2, 3, 4, 5, 6 or 7 nights. The time of usage of a therapy device for providing said therapy may also cover several weeks, including 2, 3, 4, 5, 6, 7 weeks, or several months, such as 2, 3, 4, 5, 6, 12 months or more.

According to another embodiment of the present invention, the feedback information comprises information regarding the progress and effort of the therapy.

Information regarding the progress and effort of the therapy is preferably provided in conjunction with temporal progression of the monitored vital signs. Information regarding the progress and effort of the therapy may comprise any advance in usage of the therapy, and including for instance glucose level changes, heart rate changes, blood pressure changes and/or sleep state changes.

Accordingly, the present device may provide feedback information wherein the patient is informed about the time period using the therapy in comparison to a passed time period. The patient may be informed about his progress regarding regular and/or prescribed use of the therapy. Alternatively or in addition, the feedback information may comprise information about regular and/or prescribed use of the therapy in conjunction with the vital signs and vital sign changes over time, such as (current) glucose levels and changes of the glucose levels over time. The feedback information may thus show the patient the beneficial effect of the therapy on the monitored vital sign. Patients receiving such positive feedback in visual and/or audible form may be motivated to increase their daily usage of the therapy device.

Giving the patient feedback on the usage of the therapy, the vital sign changed over time combined with information on the patients habit e.g. alcohol consume, sleep drugs, nutrition, (physical) activity are used to define with the patient goals that are planned to be achieved with the aim to bring the glucose level down, improve sleep and improve quality of life. Goal settings may comprise for example therapy usage (e.g. 6 hours a night or at least 8 hours a night), may also comprise goals like low amount of alcohol consume in the evening (e.g. only 1 glass of wine per evening), could also comprise goals like no sleep drugs, could also comprise goals on weight or goals on nutrition.

According to another embodiment of the present invention, the feedback information may comprise a representation of the therapy data over time, and vital sign data over time; and optionally other patient data over time.

The representation may be in form of a chart or any graphical representation, such as diagram using for instance a Cartesian coordinate system. For example time may be shown against vital sign data and information relating to use of the therapy. In this manner the patient may immediately recognize the effect of using the therapy on the monitored vital signs, such as glucose levels. The graphical representation may comprise sections of interest of a diagram and/or highlighting sections of interest of a diagram. In this way particular therapy results attained may be highlighted showing for instance that correct patient compliance to the therapy results in improved vital signs in comparison to cases, wherein patients' compliance with the therapy is lower.

According to a further embodiment of the present invention, the present device further comprises an electronic coaching system for coaching a patient to stay adherent to the therapy.

The electronic coaching system to coach a patient to stay adherent to a therapy, such as a CPAP or OSA therapy, may serve as a means to improve glucose level data, norepinephrine level data, heart rate data, blood pressure data and/or sleep stage data. Improving may comprise either increasing or reducing of the particular vital sign depending on the nature of the disease, such as coaching the patient to stay adherent to a therapy to reduce glucose level.

The coaching system may also serve as a means for alleviating/improving any other medical condition and/or behavioral condition reflected by respective medical data and/or behavioral data of the patient. The coaching system preferably assists in alleviating a behavioral condition reflected by respective behavioral data, such as alcohol consume, smoking, physical activities and/or nutrition, of the patient. More preferably, the coaching system assists in alleviating alcohol consume and/or smoking as alcohol consume and smoking have been both found effecting sleep apnea in a negative way. Accordingly, an effect of alcohol consume and smoking on any therapy, particularly a CPAP or OSA therapy, may be reasonably assumed. For instance, behavioral data may suggest that the patient has any particular, e.g. regular and/or frequent, behavior, such as regular and frequent alcohol consume. In that case the coaching system assists the patient in reducing alcohol consume. Alternatively, behavioral data may suggest that the patient smokes regularly and/or frequently. In that case the coaching system assists the patient in reducing smoking.

The electronic coaching system may be also based on a smartphone and optionally implemented thereon in form of an app. Alternatively or in addition, parts or all of the electronic coaching system may be implemented in form of a web based service, such as a cloud web service. Theoretical models of the behavior change, such as the transtheoretical model TTM, may be employed to optimize adherence to the therapy relating to an upper airway disorder.

The electronic coaching system preferably encompasses a module for setting goals to the patient. Goals may be set by using a smart algorithm that connects the individual's PAP adherence data to his/her glucose data. The variability seen in vital signs (such as glucose, or any other parameter) may be tied to adherence (using for instance covariance). Results are then used to set reachable goals for vital signs, such as glucose levels, that may be related to adherence. Encouraging experimentation with adherence is thereby afforded to monitor the effect of adherence on the monitored vital sign and feed back that information to the patient. Goals may reflect a small increase in current adherence levels to achieve successes (10-15% increase in time with PAP).

Alternatively or in addition, one or more rules around engagement may be implemented in the electronic coaching system. Patient interaction with the therapy device may be monitored by a program, which may be implemented as an app or as website, and trends for interaction may be identified. Such trends for interaction may include specific times or situation when a patient tends to interact. These trends may be further defined using patient's adherence data. Such interactions may be furthermore anticipated or extrapolated and useful information regarding patient's glucose monitoring and adherence may be provided.

Alternatively or in addition, data from the individual's correlation between adherence and vital sign data, such as glucose level data (and to use aggregate data from a larger pool of users eventually) may be used to project out where the patient may be in the future, such as a month, if his/her PAP use levels were at certain benchmarks. Such projection may encompass for example, "Based on your data, and the data of others with the same conditions, you would have a xx % chance of significantly reducing your blood glucose in a month if you were to use PAP therapy at least 6 hours a night".

According to a preferred embodiment of the present invention, the display unit is arranged remote from the processing unit and/or the receiving unit, and wherein the device further comprises a transmission unit for transmitting the processed therapy data and vital sign data to the display unit. The processed vital sign data preferable comprise glucose level data. Alternatively or in addition, the processed therapy data further comprise other patient data.

The display unit may comprise any optical, tactile, and/or acoustical indication means. Use of a display, such as the display of a handheld device, for instance a smartphone or tablet computer, is preferred. A plurality of display units may be used, for instance one, two, three, four or five. For instance one display unit may serve for providing/displaying the feedback information to the patient and another one to a medical practitioner. The plurality of display units may be remote from each other.

An app for e.g. a mobile phone may be used for displaying and and/or downloading feedback information. An "app" is used herein as a piece of software which can run on the internet, a computer, a mobile phone or on other electronic devices. The app may permit for instance downloading of feedback information, such as therapy data, including for instance the daily usage of a PAP therapy, and glucose level, and other patient information from a web service, such as SLEEPMAPPER™ by Philips.

The processing unit is configured to process the therapy data and vital sign data, such as glucose level data, and optionally other patient information in order to determine feedback information based on the therapy data and the vital sign data, such as glucose level data. Any number of processing units may be employed including for instance one, two, three, four or five. The processing unit may be in form of processor of a handheld device. Alternatively, the processing unit may be also in form of a web service employing for instance a website, such as SLEEPMAPPER™ by Philips. To such a web service the received vital sign data, such as glucose level data, of the patient and therapy data including information regarding the therapy of the patient, and optionally additional information received from patient questionnaires, are transmitted. The web service then provides feedback information based on the therapy data and the vital sign data, such as glucose level data, and any other data supplied to a remote display unit, such as a smartphone, to the patient. Alternatively, processing unit and display unit may be both comprised by a single device, such as a smartphone or tablet computer.

A transmission unit may be employed for transmitting the processed therapy data and vital sign data, such as glucose level data, to the display unit. Alternatively or in addition, a transmission unit may be also employed for transmitting data received by the receiving unit to a remote processing unit. This may be performed by wired or wireless signal transmission.

It is furthermore conceivable that the data as well as the feedback to the patient may be also transmitted to a caregiver, e.g. clinician, nurse, and/or a family member to view the data. Preferably, the system is adapted to have the goals set by the caregiver, e.g. clinician, in discussion with the patient.

As indicated above the number of processing units and/or display units is not particularly limited. Alternatively or in addition, the processing unit may be located remote from the receiving unit(s) and/or the processing unit(s) may be located remote from the display unit(s). Remote location requires the use of a transmission unit for transmitting respective data from either the receiving unit to the processing unit and/or processing unit to the display unit. Remote transmission is not particularly limited and includes for instance wired or wireless transmission. Wired or wireless transmission to the Internet/via Internet is particularly referred.

According to another embodiment of the present invention the device further comprises a patient interface for providing a pressurized flow of breathable gas to the patient.

Examples for such patient interfaces are: (i) nasal masks, which fit over the nose and deliver gas through the nasal passages; (ii) oral masks, which fit over the mouth and deliver gas through the mouth; (iii) full-face masks, which fit over both the nose and the mouth and deliver gas to both, and (iv) nasal pillows, which are regarded as patient interfaces as well within the scope of the present invention and which consist of small nasal inserts that deliver gas directly to the nasal passages.

A patient interface usually builds the part of a pressure support system (e.g. CPAP system) that interfaces with the patient and provides a preferably airtight seal with parts of the patient's face in order to deliver a pressurized flow of gas to the airway of the patient. Patient interface therefore normally include a patient contacting element. A patient contacting element may be understood as any component which is either in direct contact with the skin of the user and/or in vicinity thereto. The patient-contacting element may be for instance a cushion or any other skin-contacting material formed thereon. The patient-contacting element may also correspond to a mask shell and/or to its support. The skin-contacting element may be also denominated as sealing flap hereinafter.

In the above-mentioned embodiment, the patient interface may be provided with a receiving unit for receiving signals/data from an implantable glucose monitor which is based on subcutaneous amperometric technology. The glucose monitor can be also based on other detection methods such as bioimpedance spectroscopy, near infrared spectroscopy, electrochemical methods, ultrasound, electromagnetic and thermal principles, or fluorescence technology. The receiving unit may be arranged at any part of the patient interface, e.g. at the headgear, the mask shell or the cushion. Alternatively or in addition, the sensing technology, such as the sensor, can be also worn at any other position of the body, e.g. around the wrist, the ear lobe, finger, or abdomen.

Alternatively the glucometer can be a standalone system that analyzes glucose level in blood with for example amperometric technology using glucose oxidase and sending wireless the data to the receiving unit.

A patient interface may be provided for instance with a receiving unit for receiving signals/data from an implantable glucose monitor which is based on subcutaneous amperometric technology. The glucose monitor can be also based on other detection methods such as bioimpedance spectroscopy, near infrared spectroscopy, electrochemical methods, ultrasound, electromagnetic and thermal principles, or fluorescence technology. The receiving unit may be arranged at any part of the patient interface, e.g. at the headgear, the mask shell or the cushion. Alternatively or in addition, the sensing technology, such as the vital sign sensor, can be also worn at any other position of the body, e.g. around the wrist, the ear lobe, finger, or abdomen.

In case of using a glucose sensor, the patient interface may be provided in its interior with one or more means/sensors for measuring therapy data and/or sensors for monitoring a breathing gas indicative of glucose, such as acetone.

According to a preferred embodiment of the present invention, the device further comprises a vital sign sensor for measuring the vital sign data of the patient, wherein the vital sign sensor comprises: a glucose sensor for measuring the glucose level data of the patient; a norepinephrine level sensor for measuring the norepinephrine level data of the patient, a heart rate sensor for measuring the heart rate data of the patient; a blood pressure sensor for measuring the blood pressure data of the patient; and/or a sleep stage sensor for measuring the sleep stage data of the patient.

Any number of the above-mentioned sensors may be used alone or in combination with other sensors. Glucose sensors, norepinephrine sensors, heart rate sensors, blood pressure sensors and sleep stage sensors are known in the art. Examples of such sensors are outlined hereinafter. The vital sign sensor(s) may be operated in a continuous or spot-check manner.

According to still another embodiment of the present invention, the glucose sensor is a breath gas sensor for monitoring gases indicative of glucose in exhaled breath.

The kind of glucose sensor and/or the number thereof is not particularly limited. The glucose level data of the patient may be measured by using any type of known glucose sensor or blood glucose sensor. The sensor is preferably located in or in the vicinity of a therapy device, such as a mask used for ventilation therapy. In addition or alternatively, the used glucose sensor or blood glucose sensor may be either continuous or spot-check. It will be appreciated that the kind of glucose sensor employed may favor either continuous or spot-check types of measurement or both. The glucose sensors are well known in the art. Reference is made for instance to Kiera Roberts et al.: "Noninvasive monitoring of glucose levels: is exhaled breath the answer?" in J. Diabetes Sci Technol. 2012 May; 6(3): 659-664, the contents of which are included by way of reference herein in their entirety. The glucose sensor for monitoring a glucose level may be also in form of a tear sensor and positioned in the eye of the patient.

An example of a glucose sensor is a subcutaneous sensor which is preferably located immediately below the patient's skin. The implantable sensor may be, however, located at any position at the patient's body. The sensor is preferably located in the vicinity of the mask, such as below any of the mask's parts contacting the patient's skin including for instance headgears/straps and forehead support, if present. This facilitates transmission of signals/data to the present device. In general, a sensor, such as a glucose sensor or any other sensor, may transmit signals/data remotely, including for instance frequency (RF) signals and optical signals, or by wired connection.

Such subcutaneous or implantable sensors have rather small dimensions and work for sufficient periods of time and provide either continuously glucose level data or in defined time intervals. Implantable glucose sensors may be biosensors.

According to another embodiment of the present invention the glucose sensor is a standalone glucometer that analyzes glucose level in blood with for example amperometric technology using glucose oxidase. The glucose level data are preferably sent wirelessly to the receiving unit.

According to yet another embodiment of the present invention blood samples are used to determine one or more of overall glucose response, fasting glucose level, 2 hour glucose level, insulin levels, insulin sensitivity, and insulin secretion in oral glucose tolerance tests or intravenous glucose tolerance test. Alternatively or in addition, blood samples are used to determine norepinephrine level data. These blood analyzed data as vital sign data can also be sent wireless to the receiving unit to be used as input for OSA patients as feedback and to coach patients.

According to another embodiment of the present invention, the vital sign sensor is a wearable, subcutaneous or implantable sensor.

It will be appreciated that the question if the sensor is a wearable, subcutaneous or implantable sensor depends on the kind of sensor employed. A glucose sensor may be for example a wearable, subcutaneous or implantable sensor. Heart rate sensor, blood pressure sensor and sleep stage sensor are often wearable sensors. It will be, however, appreciated that the sensors, such as heart rate sensor or sleep stage sensor, are not necessarily in a wearable form. It may be advantageous to implement the heart rate sensor and/or sleep stage sensor in form of a camera to avoid disturbance of the patient.

According to a further alternative, the glucose sensor is a breath gas sensor for monitoring gases indicative of glucose in exhaled breath.

This kind of sensor may be used for monitoring a breathing gas or a constituent thereof which is indicative of the glucose level. For example, the breathing gas may be analyzed for presence and quantity of acetone. Ketone bodies may be detected. In normal individuals, there is a constant production of ketone bodies by the liver and their utilization by tissues. The concentration of ketone bodies is usually maintained in around 1 mg/dl. When the rate of synthesis of ketone bodies exceeds the rate of utilization, their concentration in increases which is known as ketonuria. This is followed by excretion of ketone bodies in urine. The overall picture of ketonuria is commonly referred as ketosis. The smell of acetone in press is a common feature of ketosis. Accordingly, detection of acetone in breath permits detection of type 1 and type 2 diabetic. In general, detecting and quantifying of acetone is correlated with glucose levels in blood. Analysis of other breathing gases on the presence of glucose is possible as well.

The breathing gas sensor may be provided for instance within the patient-interface at a position where it is subjected to air exhaled by the patient. This kind of sensor is particularly preferred since it may form part of a therapy device, i.e. installed therein, and does not cause inconvenience to the patient.

Glucose levels may be indicated (in addition to displaying on the display unit) on the CPAP mask or on any other part of the therapy system. Such an indication may be in form of a color indication for providing a coarse estimation of the glucose level, e.g. red for a critical glucose level requiring immediate intervention, yellow for warning and green to indicate glucose levels within an acceptable range, in home or hospital settings. Such an indication further permits a third person, such as a family member or a caregiver, to immediately assess the patient's glucose level at a rudimentary level. Furthermore the patient may take a look in a mirror to receive self-feedback on the actual glucose level.

According to an embodiment of the present invention, the heart rate sensor comprises an accelerometer and/or an electrocardiography sensor for acquiring the heart rate data of the patient.

Heart rate sensors are well known in the art. Any number thereof at any suitable position may be employed. The accelerometer sensor may provide a motion signal of the patient. The accelerometer sensor employed is preferably a tri-axis accelerometer known in the art. The accelerometer preferably comprises a plurality of acceleration axes and a sensor is further adapted to provide a corresponding plurality of acceleration signals. This is a possibility to determine a precise acceleration signal, since a plurality of acceleration directions are measured. The sensor may, for example, comprise a multi-axial accelerometer which is adapted to generate a movement signal indicative of the acceleration along different spatial axes. The multi-axial accelerometer is preferably a tri-accelerometer adapted to generate a movement signal that comprises three accelerometer signals indicative of acceleration along three orthogonal spatial axes, enabling for example measuring tilt and orientation changes of the subject. For example, tri-accelerometers named Bosch BMA 355, ST Microelectronics LIS3DH, LIS2HH12, ST Microelectronics LIS344ALH or Kionix KXM 52 can be used. However, also other kinds of multi-accelerometers can be used for generating accelerometer signal indicative of the acceleration along different spatial axes.

Electrocardiography or electrocardiogram (ECG) sensors measure electrical signals produced during muscle contraction. ECG sensors usually contact the patient's skin, such as chest or hand palms. Gelled and preferably dry ECG sensors may be employed.

According to another embodiment of the present invention, the sleep stage sensor comprises an accelerometer and/or a photoplethysmographic sensor for acquiring sleep stage data of the patient.

Sleep stage data, which may also comprise sleep quality data, may be provided by any kind of sensor(s). An accelerometer and photoplethysmography (PPG) sensor may be implemented in the therapy device or a part thereof, such as the patient interface. Any type of accelerometer may be employed, examples of which are indicated above. PPG sensors are known in the art.

In general, the PPG sensor is designated for enabling measuring the cardiac activity of the patient. It may be used to determine accurately inter-beat intervals and extract cardiac features needed for sleep staging. Both sensors may be implemented into the patient's interface to determine patient's body movements and cardiac activity enabling thereby determining sleep-wake statistics, including one or more of sleeping heart rate, total sleep time, sleep efficiency, number and/or duration of awakenings, but is not limited thereto. The sensors also enable to provide a patient feedback on their sleep stages, including for instance REM(R)–light (N1+N2)–Deep (N3) sleep.

Alternatively, the accelerometer and PPG sensor may be located at another body position of the patient, such as the wrist. Alternatively or in addition to the PPG sensor, an electrocardiogram (ECG) sensor may be employed for monitoring cardiac activity which is also indicative of sleep stages. Further sensors giving information on sleep stages and sleep quality include respiratory sensors, such as airflow sensors of CPAP devices. Respiratory information may be very useful for sleep staging and can complement cardiac activity. Sleep stage data and/or sleep quality data are preferably provided by an accelerometer signal, which provides limited information on sleep statistics, such as one or more of sleep-wake, total sleep time, sleep efficiency and number of awakenings, a cardiac activity signal, provided for instance by a PPG sensor. Preferably the PPG sensor is used in combination with an accelerometer. The combined use of a PPG sensor and an accelerometer has the advantage of computing the previous statistics with higher precision, and further allows sleep stages to be determined, and also arousals to be detected. Respiratory activity may be detected by an airflow sensor and optionally an accelerometer having the advantage of computing the previous statistics with higher precision, and further allows sleep stages to be determined, and also arousals to be detected. More preferably, cardiac and respiratory activity are detected (optionally, an accelerometer is used for obtaining even higher accuracy).

In general, any information on the different sleep stages including their duration and succession may be provided. The information received by the receiving unit of the present device may include one or more amount of sleep, i.e. duration of sleep, amount of deep sleep, sleep fragmentation, number of arousals and REM onset detection. This information is communicated for instance with wireless, such as RF, communication or wired communication from the receiving unit to the processing unit. This extending sensing technology enables to give patients detailed feedback on their sleep quality. It can inform the patient if he/she removed mask at a REM stage, which would be detrimental on the long-term blood sugar control. The feedback information provided and displayed to the patient may also coach the patient to try to keep the therapy in early morning hours, i.e. during a time sleep is not anymore deep and wherein the patient is more prone to disturbances caused by the therapy device, such as the patient-contacting element.

According to yet another embodiment of the present invention the blood pressure sensor comprises a sphygmomanometer and/or a PPG sensor combined with an ECG sensor for acquiring the blood pressure data of the patient.

Blood pressure data may be provided by any blood pressure sensor known in the art including for instance a sphygmomanometer or a PPG sensor combined with an ECG sensor, wherein the ECG sensor determines generation of a pressure within the heart and the PPG sensor determines arrival of the pressure wave at a location distant from the heart. The blood pressure data may be used to provide additional feedback information to the patient required for increasing patient's compliance with the therapy relating to an upper airway disorder. Preferably, sleep therapy data of the patient are received together with blood pressure data to give information to the patient on the usage time of the therapy and changes of blood pressure (e.g. longer usage of the therapy over night for several weeks opens the way to reduced blood pressure).

According to another preferred embodiment of the present invention a therapy system comprising the present device is provided.

The therapy system may comprise in addition to the present device a device for providing therapy relating to an upper airway disorder. Such a therapy device may be a device for providing ventilation therapy, including provision of pressured air and/or synthetic air for treatment of e.g. OSA or COPD and OSA, as well as respective control circuits and means for providing sensor data referring to therapy data and glucose level data of the patient and optionally one or more of a sleep stage and/or sleep quality of the patient, heart rate data, blood pressure data. The glucose level data may include one or more of overall glucose response, fasting glucose level or 2 hour glucose level or insulin levels, insulin sensitivity, insulin secretion and norepinephrine levels. The therapy data may encompass other data, e.g. habitual data and/or behavioral data, of the patient. The therapy system may be either configured to process and display the data obtained in order to determine feedback information and displaying the same with the display unit. Alternatively, the data to a remote location for processing and/or provide the data to a remote display unit.

It will be readily appreciated that the features of the present device or any combination thereof may be employed in the present method for increasing a patient's compliance with a therapy relating to an upper airway disorder and computer program. It will be further understood that the present device, system and method may be used for the treatment of a sleep disorder breathing disease and comorbidities such as diabetes or hypertension.

BRIEF DESCRIPTION OF THE DRAWINGS

These and other aspects of the invention will be apparent from and elucidated with reference to the embodiments described hereinafter. In the following drawings FIG. 1 schematically shows the main features of a device for increasing a patient's compliance with a therapy relating to an upper airway disorder;

FIG. 2b shows an exemplary implementation of the device of FIG. 2a;

DETAILED DESCRIPTION OF THE INVENTION

The present invention relates in general to any possible combination of the above-mentioned features. The detailed description is exemplified in the following with respect to glucose level data, which should not be regarded as limiting. In the same manner as indicated for glucose level data, the present system or method may be also based on norepinephrine level data. Alternatively, a combination of one or more of glucose level data and norepinephrine level data with one or more of heart rate data, blood pressure data and sleep stage data, i.e. any conceivable combination thereof, may be employed. The glucose level data may comprise data on one or more of overall glucose response, fasting glucose level, 2 hour glucose level, insulin levels, insulin sensitivity, and insulin secretion.

Figure 1:
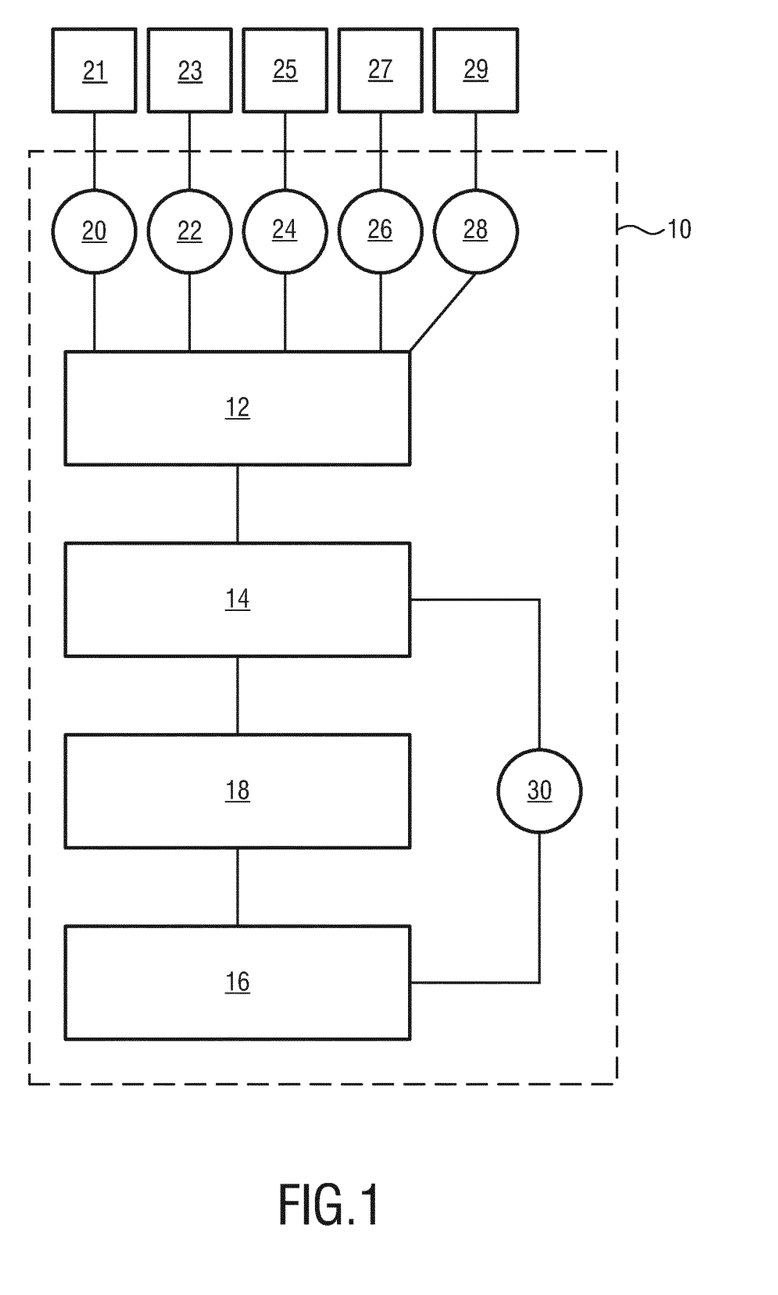

FIG. 1 schematically shows a device 10 for increasing patients' compliance with a therapy relating to an upper airway disorder. The device 10 includes a receiving unit 12, a processing unit 14, a display unit 16 and (optionally) a transmission unit 18. Receiving unit 12 receives a glucose level data 20 of the patient and therapy data 22 including information regarding the therapy of the patient. Optionally, receiving unit 12 further receives one or more of a sleep stage data and/or sleep quality data 24 of the patient, blood pressure data 26 of the patient. The glucose level data 20 may also comprise data on one or more of overall glucose response, fasting glucose level, 2 hour glucose level, insulin levels, insulin sensitivity. The receiving unit 12 may also receive other patient data 28, including one or more of habitual data and behavioral data.

Glucose level data 20 may be provided by a glucose level sensor 21. The glucose level sensor 21 may be either provide continuous measurements or may be in form of a spot-check sensor. The sensor may be based on subcutaneous amperometric technology or any other detection method, or provided as a breathing gas sensor monitoring a breathing gas, such as acetone, indicative of glucose level. In case of a breathing gas sensor it is preferably provided within a patient interface 52 as exemplarily shown in FIGS. 3 and 4.

A sensor 23 for providing therapy data 22 may be provided. Said sensor 23 may be part of a therapy system, such as a CPAP system. This sensor 23 may e.g. measure the time of usage of the CPAP system or the pressure provided by the CPAP system (over time), leakage and/or other settings of the CPAP system.

A signal indicative of sleep stages and sleep quality 24, i.e. sleep stage data and sleep quality data, may be provided by a sensor 25, such as a PPG sensor in combination with an accelerometer and/or a respiratory airflow sensor, providing the required signals.

Blood pressure data 26 may be provided by a blood pressure sensor 27 which may be in form of a sphygmomanometer or a combination of PPG sensor and ECG sensor.

Figure 5:
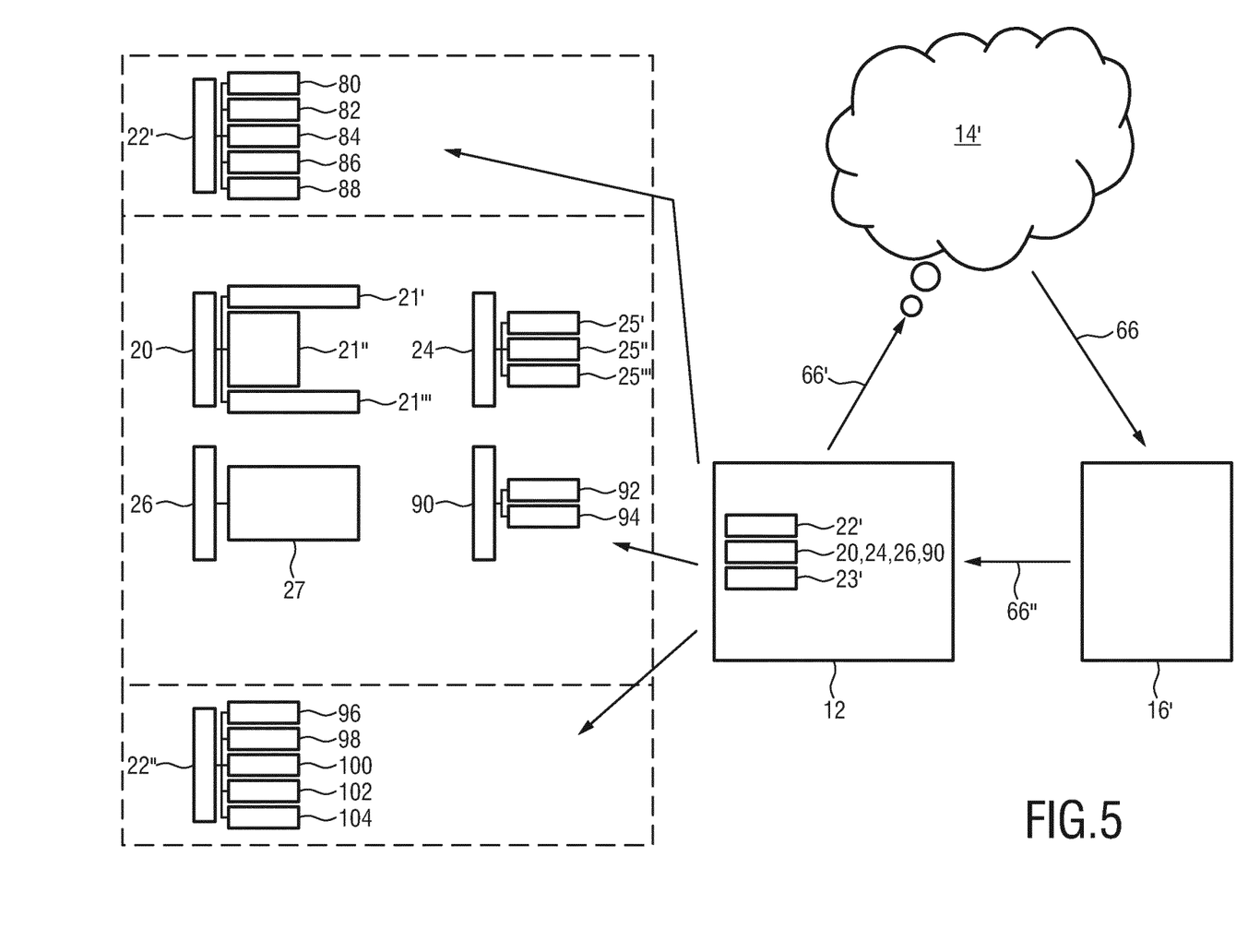
FIG. 5 schematically shows an example of a device wherein processing is performed by cloud computing.

Other patient data 28, including one or more of habitual data and behavioral data, may be provided by suitable sensors or entered by suitable input means 29, including for instance questionnaires 22' as shown in FIG. 5.

Processing unit 14 is connected with the receiving unit 12 and configured to process the therapy data 22, the glucose level data 20, the signal indicative of sleep stages and sleep quality 24, blood pressure data 26 and other patient data 28 in order to determine feedback information 30 based on the before-mentioned data. This feedback information 30 may be presented to the patient in various forms (visual, audible and/or tactile form). The feedback information 30 shall particularly indicate the beneficial effects onto the glucose level data 20 when regularly attaining and complying with the therapy. Accordingly, the patient may be motivated by the displayed feedback information 30.

The processing unit 14 provides the above-mentioned data 20, 22, 24, 26 and 28 via transmission unit 18 to display unit 16 for displaying the feedback information 30 based on the data 20, 22, 24, 26 and 28. Transmission unit 18 may be adapted for providing remote transmission. In this regard, the processing unit 14 provides a data 20, 22, 24, 26 and 28 to a remote device, such as a smartphone or tablet, provided for instant or later displaying the feedback information 30 based on the data 20, 22, 24, 26 and 28. It will be appreciated that the transmission device 18 is not necessarily required. The feedback information 30 may comprise a therapy objective, such as longer and/or more regular adherence to a therapy. Alternatively or in addition, graphical representation of the data 20, 22, 24, 26 and 28 over time may be displayed to the patient. This may be attained by displaying indication of said data over time in a conventional plot. In said graphical representation certain values, ranges of values, and/or incidents may be graphically highlighted for improved visualization. For instance the change of glucose level data 20 may be marked related to usage time of the therapy over days, weeks or months. Conscious or unconscious removal of the patient-contacting element may be determined and indicated/highlighted. Also including patient's behavior, e.g. high or low consumes of alcohol 96 related to AHI 80 (as shown in FIG. 5), and glucose level data 20 may be indicated.

Figure 2A:
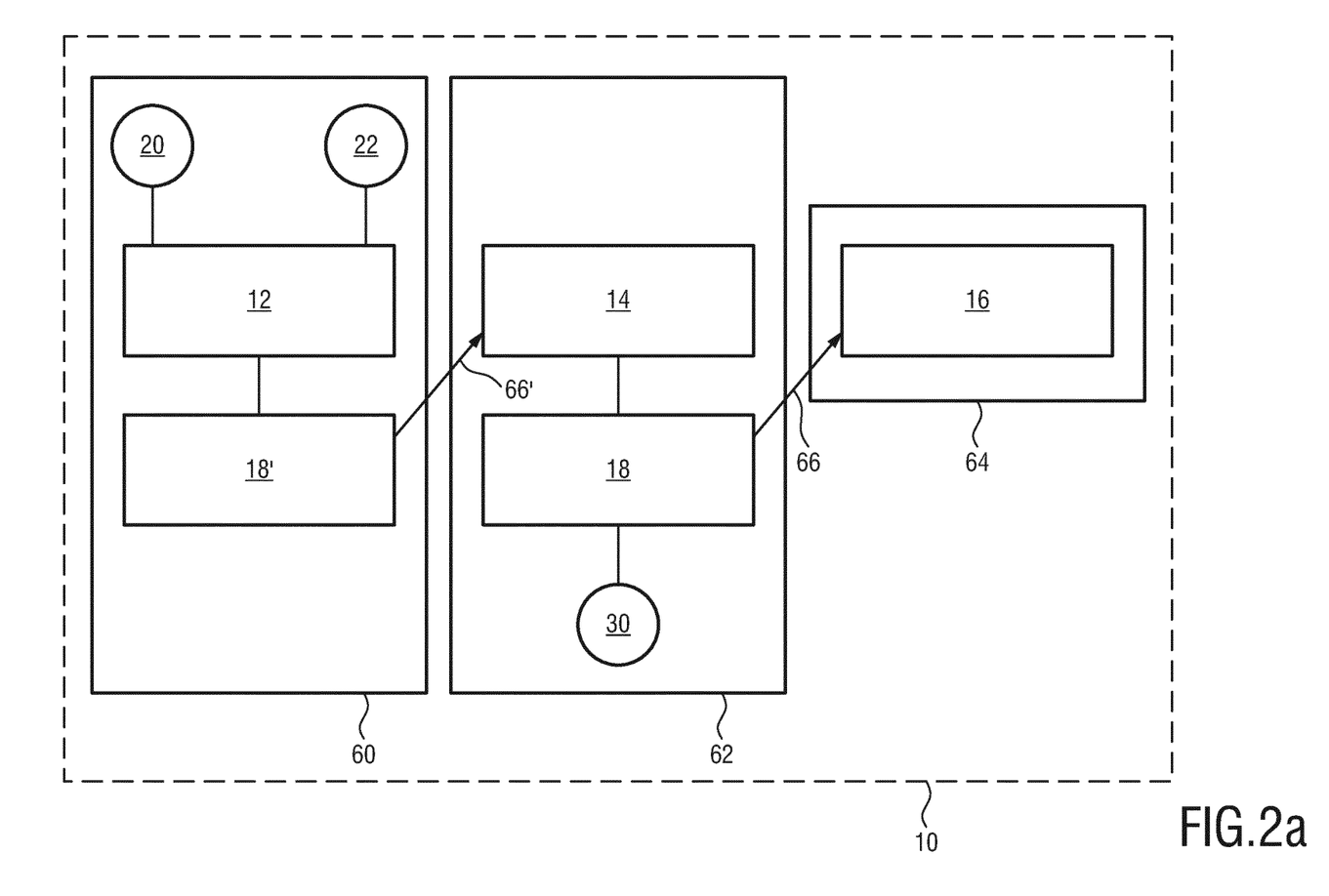
FIG. 2a schematically shows an example of a device wherein the receiving unit is remote from the processing unit and the processing unit in turn is remote from the display unit.

FIG. 2a schematically shows a device 10 for increasing patients' compliance with a therapy relating to an upper airway disorder wherein the device is split in three sections. First section 60 comprises receiving unit 12 for receiving glucose level data 20 and therapy data 22 including information regarding the therapy of the patient. Transmission unit 18' is provided for providing data 20 and 22 received by receiving unit via remote connection indicated by arrow 66' to processing unit 14 configured to process the therapy data 22 and a glucose level data 20 in order to determine patient instructions 30 based on the therapy data 22 and glucose level data 20. Processing unit 14 is connected to transmission unit 18 configured to wirelessly provide data 20 and 22 to a remote display unit 16. This is indicated by arrow 66. FIG. 2a hence encompasses the case wherein a patient adheres to a therapy relating to an upper airway disorder wherein in the first section 60 of the device 10 glucose level data 20 and therapy data 22 are received. These data are provided to a remote location, for instance a web service, which is configured to process the data 20, 22 and to determine respective feedback information 30. This is indicated by reference numeral 62. The underlying web service may be adapted to include other data 28 for the feedback information 30 as well. These other data may include respective information the patient's habit and/or behavior, which he/she has answered along questionnaires, or of other patients, such as statistical results, and/or data referring to supervision by a medical practitioner. Other patient data 28 from e.g. medical records, such as blood analysis, may include prior/old glucose level data. Prior glucose level data may encompass one or more of overall glucose response, fasting glucose level, 2 hour glucose level, insulin levels, insulin sensitivity, and insulin secretion from oral glucose tolerance tests or intravenous glucose tolerance test. Prior vital sign data may also encompass previously determined and recorded data on norepinephrine levels and/or any other vital sign data.

Feedback information 30 is then provided to section 64 for providing/displaying the feedback information 30 to the patient by the display unit 16 of a smartphone or tablet computer. This may be accomplished by an appropriate app.

Figure 2B:
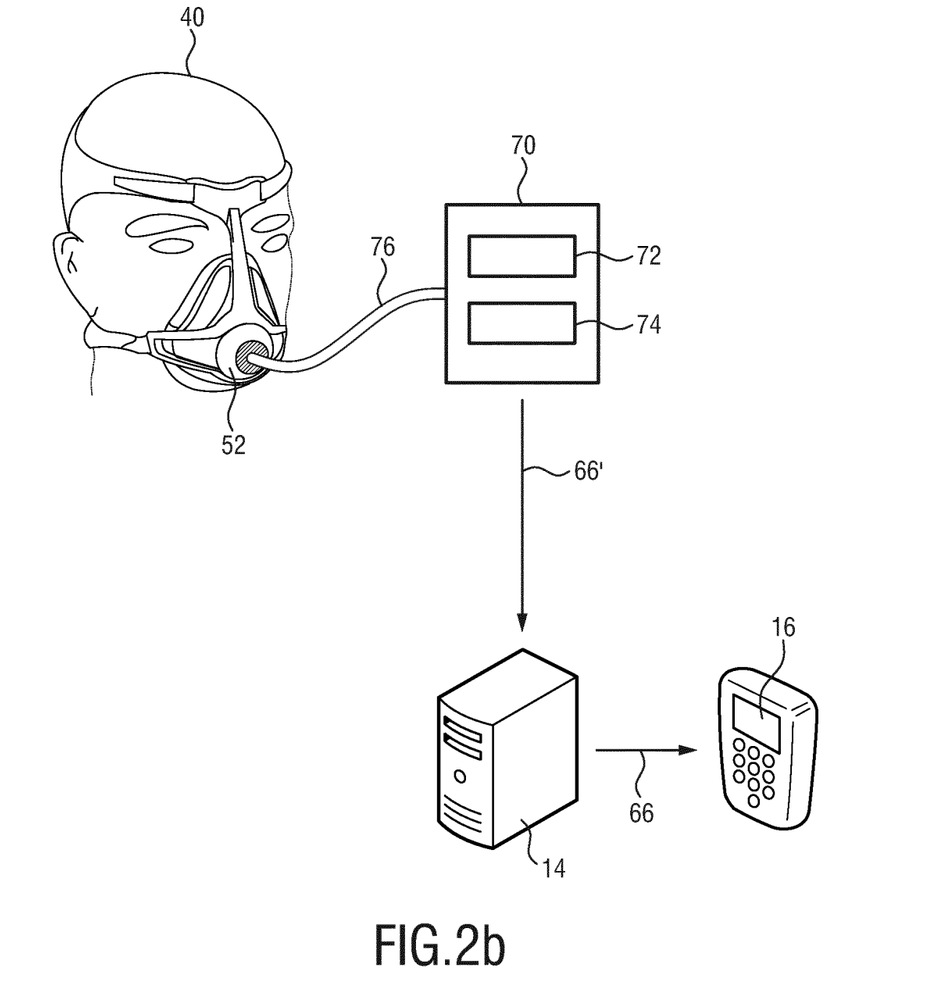

FIG. 2b shows an exemplary implementation of the device of FIG. 2a. Patient 40 wears a patient interface 52 and is connected via a pressure line 76 (e.g. a hose) to a PAP system 70 in order to receive a PAP therapy. PAP system 70 comprises a pressure device 72 for providing the required pressurized flow of breathable gas via the hose 76 and patient interface 52 to the patient 40. The patient interface 52 is further provided with a breath gas sensor 21' for monitoring acetone (see e.g. FIG. 4). Of course, other types of glucose sensors 21 may be used as well, as mentioned before. The signals of the sensor 21, 21' are preferably transmitted wireless to the control circuit 74 of PAP system 70.

PAP system 70 also generates therapy data 22 derived from (i) system settings and (ii) one or more sensors of the system 70 for measuring system related parameters, such as a pressure sensor for measuring the pressure provided to the patient. The control circuit 74 (i.e., a receiving unit for receiving, via the one or more sensors, glucose level data and therapy data and a transmission unit) transmits glucose level data 20 and therapy data 22 to a remote processing unit 14 (e.g. a server). Data transmission may be performed via the internet, as indicated by arrow 66'. The processing unit 14 processes the therapy data 22 and the glucose level data 20 in order to determine feedback information based on the therapy data 22 and the glucose level data 20. The processing unit 14 may be implemented in form of a web service. The feedback information may then be further transmitted via internet to a mobile device comprising a display 16, as indicated by arrow 66. The web service may assist patient 40 in enhancing the sleep therapy experience and may provide quick and easy access to sleep therapy results and their impact onto the measured glucose level of the patient 40.

The embodiment shown in FIG. 2 shows the particular advantage associated with the usage of a remote web service for assessment the feedback information 30 for increasing patient's compliance with the therapy.

Figure 3:
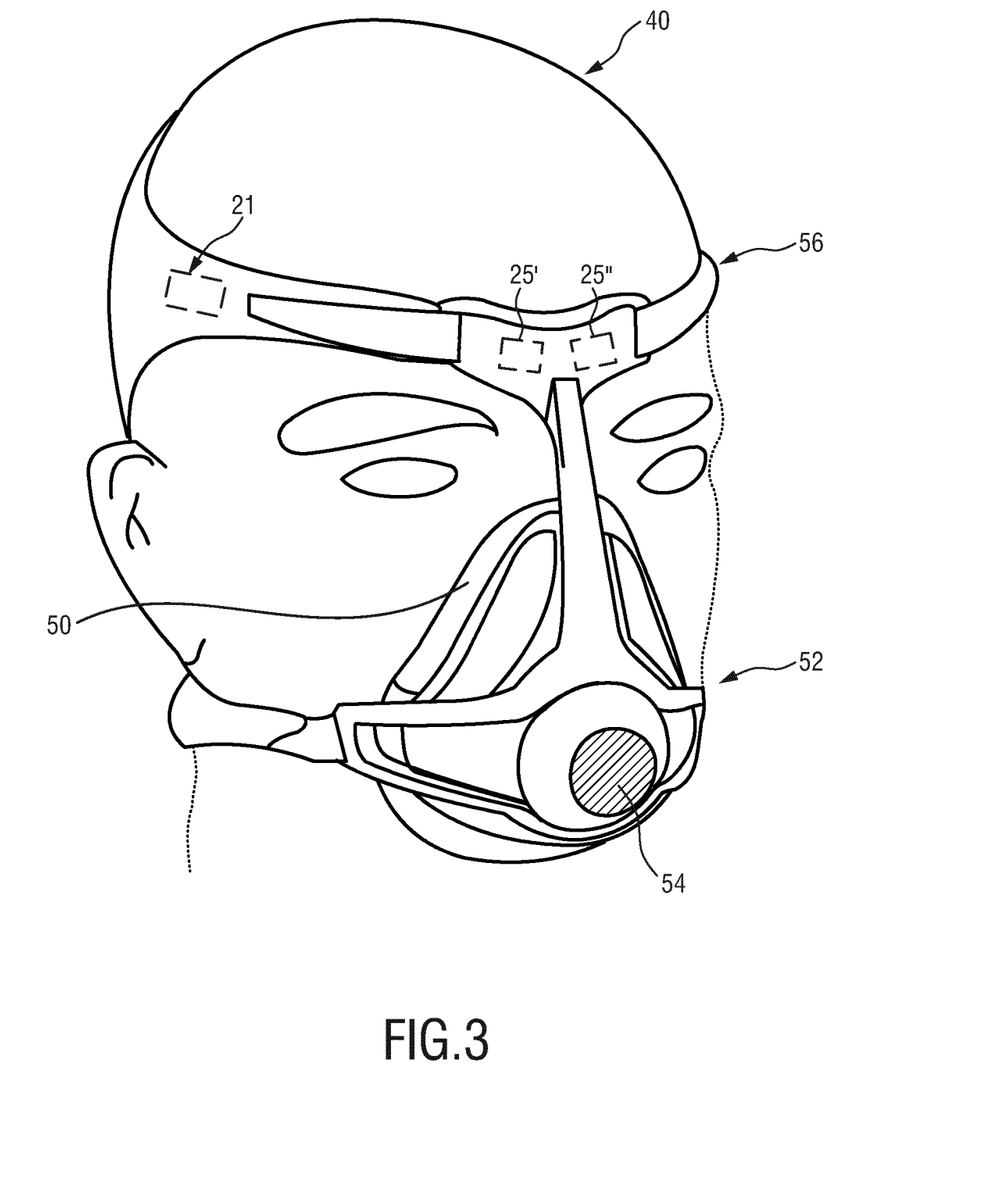
FIG. 3 shows an example of a patient interface according to the present invention.

FIG. 3 shows an example of a patient interface for providing a flow of breathable gas. The patient interface is in FIG. 3 in its entirety is denoted with reference numeral 52. The patient interface 52 is typically used in pressure support systems (e.g. CPAP systems). Such patient interfaces 52 are known and are mostly worn on the head using a strap system around the head of the patient 40 to hold a mask in place around the airway entry features of the human face. The patient interface 52 typically comprises a rigid or semi-rigid mask shell to which the headgear/strap system is attached. The mask shell is usually made of a rigid or semi-rigid material, such as e.g. plastic, polycarbonate or silicon. However, also other materials are generally conceivable. The mask shell serves as holding frame for holding a flexible soft cushion/mask flap, also referred to as patient-contacting element 50. Patient-contacting element 50 engages the patient's face during use. It serves as mask-to-patient interface for providing a pressurized flow of breathable gas to a patient 40. The patient-contacting element 50 may be made for instance from polycarbonate and provided with a breathing gas sensor therein for determining glucose levels (not shown). The main structural elements of the patient-contacting element 50 are generally known.

These patient-contacting elements or cushions 50 are made in the art of silicon and comprise one or more gel pads in order to establish a soft contact on the patient's face. A further function of these cushions 50 is the sealing of the interior of the patient's interface 52 to the exterior surrounding in order to prevent air leaks between the patient's interface 52 and the patient's face when pressure is applied to the patient's airway. The shape of the cushion/mask flap 50 is thereto preferably adapted to the shape of the user's face. The patient-contacting element 50 may not only be embodied in form of a cushion, but may be also in form of a forehead-pad, a headgear 56 and a cheek-mounted support.

In addition to a respective inlet for pressurized air 54, the forehead pad including strap 56 comprises PPG sensor 25' provided in direct contact with patient's 40 skin and accelerometer sensor 25" at any position thereon. In addition, glucose sensor 21 is shown. Glucose sensor 21 may comprise a subcutaneous sensor implanted at a respective location directly below patient's 40 skin. In the forehead pad/headgear/strap 56 a device is located for receiving the signals provided by sensor 21. Data provided by sensors 21, 25' and 25" are provided together with therapy data (not shown) to a processing unit and display unit for displaying respective feedback information.

Figure 4:
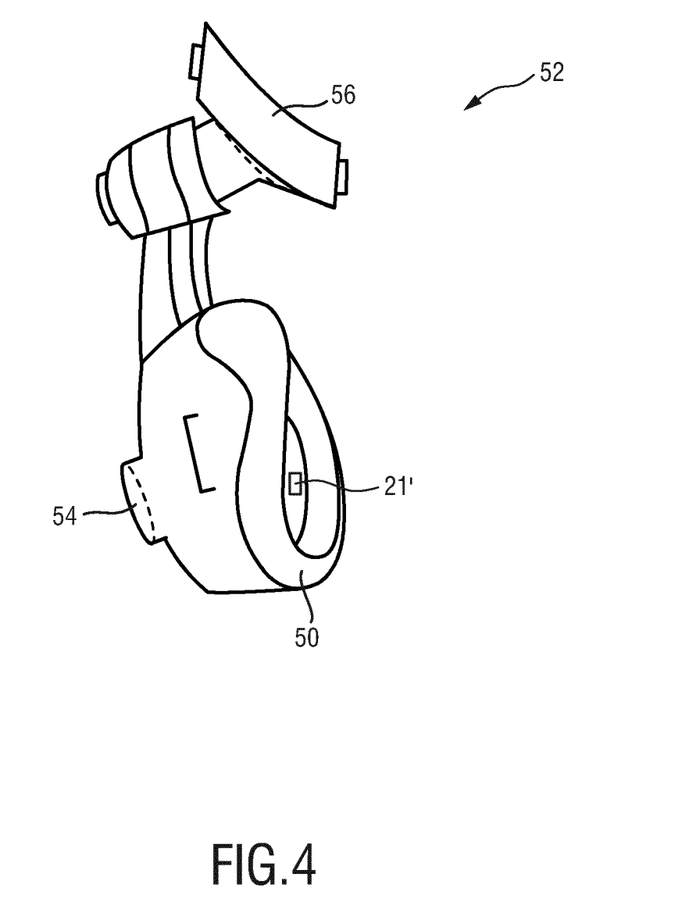
FIG. 4 schematically illustrates a side view of a patient interface.

An example illustrated in FIGS. 3 and 4 refers to a so-called full face mask 52 wearing the cushion/mask flap 50 surrounds the nose and the mouth of the user 40. These full-face masks often comprise an additional cushion support 56 referred to as forehead support 56, which may be integrally connected to the mask shell, and which is arranged to engage the forehead of the patient 40. The additional cushion support/forehead support 56 mainly serves to balance the forces that a mask 52 exerts on the face of the patient 40 and is mechanically stabilized to the mask shell as well as to serve or correct a comfortable fit of the mask. In addition, forehead support 56 may be provided with one or more sensors such as sensors 21, 25' and 25". A gas supply hose (not shown) is usually connected to a connection interface 54 that is preferably attached or integrated into the mask shell. The mask may include the patient-contacting element 50 according to the present invention. Patient-interface 52 is provided with a glucose level sensor 21' for monitoring a breath gas indicative of glucose, such as acetone.

FIG. 5 shows a device 10 wherein processing is performed by cloud computing. Cloud 14' for cloud computing may be the digital health suite by Philips. The cloud 14' receives CPAP 22' data, data of various sensors 20, 24, 26, 90 and entries into questionnaires 22" manually entered from patient 40 may also comprise other data including one or more data on overall glucose response, fasting glucose level, 2 hour glucose level, insulin levels, insulin sensitivity, and insulin secretion from oral glucose tolerance tests or intravenous glucose tolerance test. CPAP data 22' encompass data about AHI 80, mask fit 82, mask usage 84, flow parameters 86 and pressure data 88. Sensor comorbidity options are provided in form of glucose level data 20, blood pressure data 26 (including information about hypertension) provided as an integrated sensor or as a separate device, a signal indicative of sleep stages and sleep quality 24 and potentially present other sensors and services 90. The glucose level data 20 is provided by a glucometer 21', a subcutaneous sensor 21", or a non-invasive wearable sensor 21''' which may be a sensor integrated in the mask or a non-integrated sensor. Blood pressure data 26 are provided by blood pressure sensor 27. The signal indicative of sleep stages and sleep quality 24 is provided by PPG sensor 25' and accelerometer 25" affording cardiac inter-beat interval 25'''. Potentially present other sensors and services 90 include oxygen saturation sensor 92 and powersleep 94 (audio and EEG). Patient lifestyle and profile information are afforded by entering patient habits/behavior data 22"'. This may be performed by questionnaire 22" posing required questions to the patient 40 about one or more of alcohol consume 96, drug usage 98, nutrition 100, phenotype 102 and other relevant information 104 including for instance (disease) symptoms or information about general discomfort. Potentially other data may also comprise other patient data 28, such as prior glucose level data including one or more data on overall glucose response, fasting glucose level, 2 hour glucose level, insulin levels, insulin sensitivity, and insulin secretion from oral glucose tolerance tests or intravenous glucose tolerance test. The data gathered by integrated or non-integrated sensors 20, 24, 26 and 90 as well as information about CPAP usage 22' and manually entered information on patient habits/behavior and other patient data are transmitted (as indicated by arrow 66') to Philips digital health suite 14' for evaluation, i.e. for processing for determining feedback information 30. The feedback information 30 may further comprise patient coaching and is provided to patient's mobile phone 16' (as indicated by arrow 66). Patient 40 further interacts (66") with the receiving unit 12 to control for instance CPAP therapy, to select the one or more sensors employed, and/or directly receive data from the sensor(s).

Having explained the possible components and system architecture of device 10, in the following preferred implementations are exemplified:

In a first embodiment a glucose sensor 21 is used which may be based on amperometric measurements with a tiny electrode that is subcutaneous positioned under the skin of a patient 40 to measure glucose levels 20 in tissue fluid or a sensor not subcutaneous based on detection methods such as bioimpedance spectroscopy, near infrared spectroscopy, electrochemical methods, ultrasound, electromagnetic and thermal principles, fluorescence technology or provided in the eye as tear sensor. Signals 20 are received by a transmitter which is mounted on the headgear 56 of a sleep apnea mask 52. The transmitter sends the information via wireless radio frequency to a monitoring and display device 16. The sleep apnea mask 52 and CPAP system 70, which the patient 40 is using, are linked to a mobile application and website. The glucose level data 20 as well as usage of the CPAP therapy 22 can be downloaded by the patient 40 via an app from his/her mobile phone. This may include patient's daily feedback on the time he/she used CPAP therapy device 70, but it may also comprise the glucose level data 20. The device 10 may e.g. demonstrate the patient 14 the glucose level data 20 from night to night and the related usage of the CPAP system 70 in a graphical representation. The service may give the patient 40 feedback information 30 when he/she removed the mask 52 in the night. The patient 40 may also get coaching to stay adherent to the therapy or may receive a feedback whether he/she achieved a therapy goal that has been set in advance.

In a second embodiment a glucose sensor 21' is used which may be in the form of a breath gas sensor for monitoring a breath gas indicative of glucose. The glucose sensor 21' is mounted to the patient interface 52. The sensor 21' is connected to a transmitter that sends the information via wireless radio frequency to a monitoring and display device 16. The patient interface 52 and CPAP system 70, which the patient 40 is using, are linked to a mobile application and website in order to transfer the therapy data 22. The glucose level data 20 as well as the CPAP usage data 22 (therapy data) can be downloaded by the patient 40 via an app from his/her mobile phone. This includes patient's daily feedback on the time he/she used the CPAP system 70, but it also comprises the glucose level data 20. The present device 10 demonstrates the patient the glucose level data 20 from night to night after time and the related usage data 22 of the CPAP system 70. The service may e.g. give the patient 40 information when he removed the mask 52 in the night, which results in lower usage time and which consequences a lower usage onto his/her glucose level. The patient 40 may also receive coaching to stay adherent to the therapy.

In a third embodiment a glucose sensor 21 is based on amperometric measurements with a tiny electrode which is subcutaneous positioned under the skin to measure glucose levels 20 in tissue fluid or a sensor not subcutaneous based on detection methods such as bioimpedance spectroscopy, near infrared spectroscopy, electrochemical methods, ultrasound, electromagnetic and thermal principles, fluorescence technology or provided in the eye as tear sensor. The sensor 21 is mounted in any position on the body. The sensor 21 is connected to a transmitter that sends the information via wireless radio frequency to a monitoring and display device 16. The sleep apnea mask 52 and CPAP system 70, which the patient 40 is using, are linked to a mobile application and website. The glucose level data 20 as well usage data 22 of the CPAP therapy can be downloaded by the patient 40 via an app from his mobile phone. This includes patient's daily feedback on the time he/she used the mask 52 but it also comprises the glucose level data 20. The present device 10 demonstrates the patient 40 the glucose level data 20 from night to night and the related usage data 22 of the CPAP system 70. The service gives the patient 40 information when he/she removed the mask in the night. The patient 40 gets coaching to stay adherent to the OSA therapy to prevent increase of glucose level data 20 and treat apnea.

In a fourth embodiment glucose level data, such as data on overall glucose response, fasting glucose level, 2 hour glucose level, insulin levels, insulin sensitivity, and/or insulin secretion from oral glucose tolerance tests or intravenous glucose tolerance test, are used. The data are sent via wireless radio frequency to a monitoring and display device 16. The sleep apnea mask 52 and CPAP system 70, which the patient 40 is using, are linked to a mobile application and website. The vital sign data as well usage data 22 of the CPAP therapy can be downloaded by the patient 40 via an app from his mobile phone. This includes patient's daily feedback on the time he/she used the mask 52 but it also comprises the vital sign data.

In the fifth embodiment, next to the continuous glucose sensor 21 an accelerometer 25" and a photoplethysmography (PPG) sensor 25' are implemented in the mask 52 for example in the forehead pad 56 or any other position in the mask 52. It will be, however, appreciated that the accelerometer 25" and the PPG sensor 25' are not necessarily implemented in the mask 52. The PPG sensor 25' enables to measure in the mask 52 patient's cardiac activity. It can be used to determine accurately inter-beat intervals and to extract cardiac features, i.e. signals indicative of sleep stages and/or sleep quality 24. Both sensors 25' and 25" are implemented into the patient interface 52 to determine patient's body movements and cardiac activity and enable in this way to determine sleep-wake statistics (sleeping heart rate, total sleep time, sleep efficiency, number & duration of awakenings). The sensors 25' and 25" enable also to give patients feedback data 30 on their sleep stages REM (R) Light (N1+N2) Deep (N3) sleep. The patient feedback 30 about amount of sleep, amount of deep sleep, sleep fragmentation, number of arousals, REM onset detection as well as glucose level is communicated via RF communication or any other communication technology, via the display unit 16, to the patient 40. The data 30 can for example be downloaded by the patient via an app from his mobile phone. This extending sensing technology enables the present device 10 to give a patient detailed feedback on sleep quality. It can inform the patient if the mask has been removed at the REM stage, which would be detrimental to his/her sleep quality. The present device 10 can also coach the patient 40 to try to keep the mask 52 in the early morning hours of the night on.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for increasing a patients compliance with a therapy relating to an upper airway disorder, comprising:
    a patient interface for providing a pressurized flow of breathable gas;
    a positive airway pressure device including a control circuit for administering the therapy, via the patient interface, and for receiving, via multiple respective sensors, both (i) vital sign data that includes glucose level data and norepinephrine level data, and (ii) therapy data that includes information regarding the therapy;
    a processing unit for determining adherence feedback information in response to both (i) the therapy data and (ii) the vital sign data, wherein the adherence feedback information includes adherence guidance/coaching information configured to guide/coach the patient to stay adherent to the therapy for improving a given glucose level in which a variability in the given glucose level is tied to an adherence to the therapy relating to the upper airway disorder, wherein the processing unit is further for determining a measure of increased adherence based on a lowering of a current glucose level from a previous higher glucose level in the glucose level data; and
    a display unit for displaying the adherence feedback information, wherein the adherence feedback information further includes a compliance impact indicator indicative of an impact onto the current glucose level, wherein the compliance impact indicator is (i) positive for the current glucose level being lowered in response to regularly attaining and complying with the therapy, and (ii) negative for the current glucose level being raised in response to not regularly attaining and complying with the therapy.

2. The device of claim 1, wherein the vital sign data further include one or more of heart rate data, blood pressure data and sleep stage data of the patient.

3. The device of claim 1, wherein the therapy data include one or more of an apnea-hypopnea-index, a number of sleep apneas per night, and a time of usage of a therapy device for providing said therapy.

4. The device of claim 1, wherein the adherence feedback information further comprises information regarding a progress and effort of the therapy.

5. The device of claim 1, wherein the adherence feedback information further comprises a representation of the therapy data over time, and the vital sign data over time.

6. The device of claim 1, wherein the multiple respective sensors each include a vital sign sensor for measuring vital sign data, wherein the vital sign sensor is selected from among the group consisting of:
- a glucose sensor for measuring glucose level data;
- a norepinephrine sensor for measuring norepinephrine level data;
- a heart rate sensor for measuring heart rate data;
- a blood pressure sensor for measuring blood pressure data; and/or
- a sleep stage sensor for measuring sleep stage data.

7. The device of claim 6, wherein the glucose sensor is a wearable, subcutaneous or implantable sensor.

8. The device of claim 6, wherein the glucose sensor is a breath gas sensor for monitoring gases indicative of glucose in exhaled breath.

9. The device of claim 6, wherein the glucose sensor is arranged at the patient interface.

10. The device of claim 6, wherein the heart rate sensor comprises an accelerometer and/or an electrocardiography sensor for acquiring the heart rate data.

11. The device of claim 6, wherein the sleep stage sensor comprises an accelerometer and/or a photoplethysmographic sensor for acquiring the sleep stage data.

12. A method for increasing a patient's compliance with a therapy relating to an upper airway disorder, comprising:
- administering the therapy, via a patient interface for providing a flow of breathable gas and a positive airway pressure device including a control circuit, and receiving, via multiple respective sensors, both (i) vital sign data that includes glucose level data and norepinephrine level data, and (ii) therapy data that includes information regarding the therapy;
- processing, via a processing unit, both (i) the therapy data and (ii) the vital sign data to determine adherence feedback information in response to both the therapy data and the vital sign data, wherein the adherence feedback information includes adherence guidance/coaching information configured to guide/coach the patient to stay adherent to the therapy for improving a given glucose level in which a variability in the given glucose level is tied to an adherence to the therapy relating to the upper airway disorder, further to determine a measure of increased adherence based on a lowering of a current glucose level from a previous higher glucose level in the glucose level data; and
- displaying, via a display unit, the adherence feedback information, wherein the adherence feedback information further includes a compliance impact indicator indicative of an impact onto the current glucose level, wherein the compliance impact indicator is (i) positive for the current glucose level being lowered in response to regularly attaining and complying with the therapy, and (ii) negative for the current glucose level being raised in response to not regularly attaining and complying with the therapy.

13. A non-transitory computer readable medium embodied with executable computer program code for causing a computer or a processor to carry out the steps of the method as claimed in claim 12 when said computer program code is executed on the computer or the processor.

* * * * *